US00PP24097P2

(12) United States Plant Patent
Bergman

(10) Patent No.: US PP24,097 P2
(45) Date of Patent: Dec. 17, 2013

(54) ***CHRYSANTHEMUM* PLANT NAMED 'CIDZ0032'**

(50) Latin Name: *Chrysanthemum×morifolium*
Varietal Denomination: CIDZ0032

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 67 days.

(21) Appl. No.: 13/506,882

(22) Filed: May 22, 2012

(51) Int. Cl.
*A01H 5/00* (2006.01)

(52) U.S. Cl.
USPC ..... Plt./293

(58) Field of Classification Search
USPC ..... Plt./293
See application file for complete search history.

*Primary Examiner* — Annette Para
(74) *Attorney, Agent, or Firm* — Joshua L. Price

(57) ABSTRACT

A new *Chrysanthemum* plant named 'CIDZ0032' particularly distinguished by the red decorative-type inflorescences, strong vigorous growth with good branching, excellent flowering uniformity with an 8 week flowering response.

1 Drawing Sheet

Latin name of the genus and species of the plant claimed: *Chrysanthemum×morifolium.*

Varietal denomination: 'CIDZ0032'.

BACKGROUND OF THE NEW PLANT

The present invention comprises a new *Chrysanthemum*, botanically known as *Chrysanthemum×morifolium*, and hereinafter referred to by the variety name 'CIDZ0032'.

'CIDZ0032' is a product of a planned breeding program. The new cultivar has red decorative-type inflorescences, strong vigorous growth with good branching, excellent flowering uniformity with an 8 week flowering response.

'CIDZ0032' originated from a hybridization made in January 1998 in a greenhouse in Salinas, Calif. The female parent was an unpatented, proprietary plant designated 'YB-6351'. 'YB-6351' has light pink spoon shaped inflorescences and a slower flowering response than 'CIDZ0032'.

The male parent of 'CIDZ0032' was a proprietary, unpatented plant identified as 'YB-6605' with bronze-red, single form, spoon-type inflorescences.

The resultant seed was sown in a shade structure in July 1998 in Fort Myers, Fla. 'CIDZ0032' was selected as one flowering plant within the progeny of the stated cross in December 1998, grown in pots under a shade structure in Fort Myers, Fla.

The first act of asexual reproduction of 'CIDZ0032' was accomplished when vegetative cuttings were propagated from the initial selection in March 1999 in a greenhouse in Fort Myers, Fla.

BRIEF SUMMARY OF INVENTION

Horticultural examination of plants grown from cuttings of the plant initiated in March 1999, and continuing thereafter, has demonstrated that the combination of characteristics as herein disclosed for 'CIDZ0032' are firmly fixed and are retained through successive generations of asexual reproduction.

'CIDZ0032' has not been observed under all possible environmental conditions. The phenotype may vary significantly with variations in environment such as temperature, light intensity, and day length.

A Plant Breeder's Right for this cultivar was applied for in Canada on Jul. 29, 2011, No. 11-7348. 'CIDZ0032' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIDZ0032' with colors being as true as possible with an illustration of this type.

Figure 1:
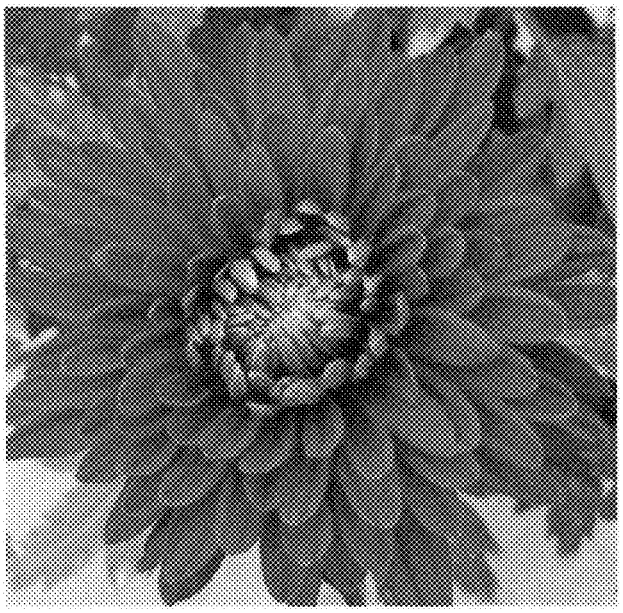
Figure 2:
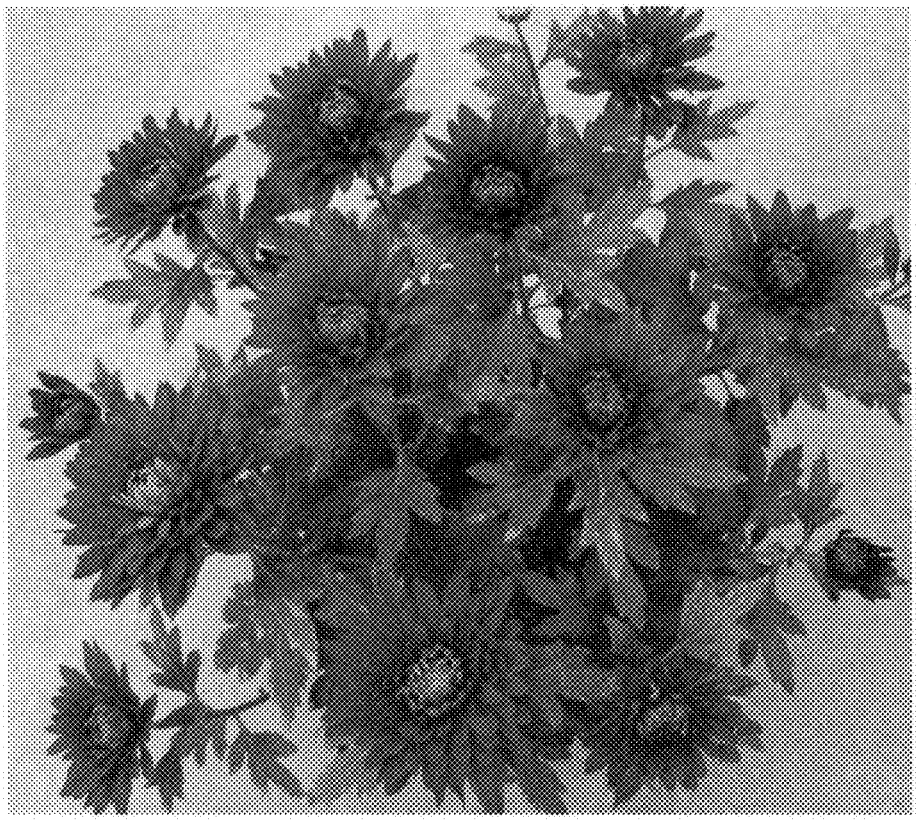

The photographic drawings show in FIG. 1 a close-up of the flowers and in FIG. 2, 4 flowering plants of the new variety.

DETAILED BOTANICAL DESCRIPTION

The plant descriptions, measurements and aforementioned photographs were taken in Gilroy, Calif. in January 2012 under natural light. These plants were grown disbudded, 4 plants in a 5 inch pot under blackcloth controlled greenhouse trial conditions in Gilroy, Calif. These plants were 10-12 weeks old.

Color references are made to The Royal Horticultural Society Colour Chart (R.H.S.) 2001.

TABLE 1

DIFFERENCES BETWEEN THE NEW VARIETY 'CIDZ0032' AND A MOST SIMILAR VARIETY

| | 'CIDZ0032' | 'Yotobago' (U.S. Plant Pat. No. 15,412) |
|---|---|---|
| Inflorescence size: | Larger | Smaller |
| Inflorescence color: | Darker red | Lighter red |
| Flowering response time: | 1 week faster | 1 week slower |

Plant:

*Form, growth and habit.*—Herbaceous pot-type, stems upright, good branching, strong and moderately vigorous growth habit with good flowering uniformity.

*Plant height*.—About 25.0 cm.
*Plant height* (*inflorescence included*).—29.0-33.0 cm.
*Plant width*.—20.0-24.0 cm.

Roots:
*Number of days to initiate roots*.—About 4 days at about 22 degrees C.
*Number of days to produce a rooted cutting*.—About 10 days at 22 degrees C.
*Type*.—Fine, fibrous, free branching.
*Color*.—RHS N155B but whiter.

Foliage:
*Arrangement*.—Alternate.
*Immature, leaf color, upper surface*.—Closest to RHS 147A.
*Lower surface*.—RHS 147B but more green.
*Mature, leaf color, upper surface*.—Closest to RHS 147A.
*Lower surface*.—RHS 147B but more green.
*Length*.—6.7-7.5 cm.
*Width*.—4.5-5.3 cm.
*Shape*.—Ovate.
*Base shape*.—Attenuate.
*Apex shape*.—Mucronulate.
*Margin*.—Palmately lobed, irregularly incised and serrate.
*Texture, upper surface*.—Bifid T-shaped hairs.
*Lower surface*.—Bifid T-shaped hairs.
*Color of veins, upper surface*.—RHS 147C.
*Color of veins, lower surface*.—RHS 147C.
*Pattern of veining*.—Palmate.
*Petiole color*.—RHS 147C.
*Length*.—2.2-3.0 cm.
*Diameter*.—0.25 cm.
*Texture*.—Bifid T-shaped hairs.

Stem:
*Quantity of main branches per plant*.—4-5.
*Color of stem*.—RHS 146A but appears lighter due to hair.
*Length of stem*.—20.0-25.0 cm.
*Diameter*.—0.4-0.5 cm.
*Length of internodes*.—0.5-2.0 cm.
*Texture*.—Bifid T-shaped hairs.
*Color of peduncle*.—RHS 146A but appears lighter due to hair.
*Length of peduncle*.—3.0-3.5 cm.
*Peduncle diameter*.—0.4 cm.
*Texture*.—Bifid T-shaped hairs.

Inflorescence:
*Type*.—Compositae type, solitary decorative-type inflorescences, borne terminally above foliage, ray florets arranged acropetally on a capitulum.
*Quantity of short days to flowering* (*response time*).—About 8 weeks.
*Natural season flowering*.—Not determined on this variety.
*Quantity of inflorescences per plant*.—3-4.
*Lastingness of individual blooms on the plant*.—About 4 weeks.
*Fragrance*.—Slightly spicy.

Bud (just when opening/showing color):
*Color*.—Between RHS 183C and RHS 183D.
*Length*.—1.9-2.5 cm.
*Width*.—1.7-2.4 cm.
*Shape*.—Broadly oblate.

Immature inflorescence:
*Diameter*.—7.0-7.5 cm.
*Color of ray florets, upper surface*.—Closest to RHS 185A but deeper more velvety.
*Lower surface*.—RHS 162C with longitudinal bars of RHS 180A towards the apex and on margins.

Mature inflorescence:
*Diameter*.—10.0-11.0 cm.
*Depth*.—3.0-3.5 cm.
*Total diameter of disc*.—Indistinct to date.
*Receptacle color*.—Closest to RHS 144B.
*Receptacle height*.—0.5 cm.
*Receptacle diameter*.—0.7 cm.

Ray florets:
*Average quantity of florets*.—Approximately 225 in several whorls.
*Color of florets, upper surface*.—Closest to RHS 53A but deeper and a little more purple hue.
*Lower surface*.—RHS 162B heavily overlaid with RHS 181C to RHS 181D in a slight cross-hatched like plaid pattern.
*Length*.—4.1-5.1 cm.
*Width*.—0.9-1.1 cm.
*Shape*.—Elliptical.
*Apex shape*.—Obtuse.
*Base shape*.—Cuneate.
*Margin*.—Entire.
*Texture, upper surface*.—Papillose.
*Lower surface*.—Papillose.

Disc florets:
*Average quantity of florets*.—About 4-6, are very immature to date.
*Color of florets*.—RHS 155C with about RHS 1B at apex.
*Length*.—0.2 cm.
*Width*.—0.05 cm.
*Shape*.—Tubular, elongated.
*Apex shape*.—Acute, 5 pointed.
*Texture, inner surface*.—Glabrous.
*Outer surface*.—Glabrous.

Phyllaries:
*Quantity*.—About 20 with additional bracts amongst the ray florets.
*Color, upper surface*.—RHS 137A but appears lighter due to hair.
*Lower surface*.—RHS 137A.
*Length*.—0.6-1.0 cm.
*Width*.—0.2-0.25 cm.
*Shape*.—Lanceolate.
*Apex shape*.—Acute.
*Base*.—Fused.
*Margins*.—Entire; some papery.
*Texture, upper surface*.—Glabrous.
*Lower surface*.—Bifid T-shaped hairs.

Reproductive organs:
*Pistil*.—1, found on both types of florets.
*Length*.—0.3 cm.
*Style color*.—RHS 155C.
*Style length*.—0.2 cm.
*Stigma color*.—RHS 1C.
*Stigma shape*.—Bi-parted.
*Ovary color*.—RHS 155C but a little more green.
*Ovary length*.—0.05 cm.
*Ovary width*.—0.05 cm.
*Stamens*.—4, found on only on the disc florets.
*Color of filaments*.—RHS 155C.

*Length filaments*.—0.3-0.4 cm.
*Anther color*.—RHS 15C.
*Anther length*.—0.1 cm.
*Anther shape*.—Oval.
*Color of pollen*.—RHS 21A.
*Pollen amount*.—Poor.
*Fertility/seed set*.—Has not been observed to date.
*Disease/pest resistance*.—Has not been observed to date.

What is claimed is:

1. A new and distinct variety of *Chrysanthemum* plant named 'CIDZ0032' substantially as illustrated and described herein.

* * * * *